(12) United States Patent
Brunner

(10) Patent No.: US 10,143,448 B2
(45) Date of Patent: Dec. 4, 2018

(54) MEDICAL DEVICE COMPRISING A CURVED NEEDLE

(71) Applicant: Philippe Brunner, Frères (MC)

(72) Inventor: Philippe Brunner, Frères (MC)

( * ) Notice: Subject to any disclaimer, the term of this patent is extended or adjusted under 35 U.S.C. 154(b) by 0 days.

(21) Appl. No.: 15/608,029

(22) Filed: May 30, 2017

(65) Prior Publication Data

US 2017/0311934 A1    Nov. 2, 2017

Related U.S. Application Data

(62) Division of application No. 14/436,704, filed as application No. PCT/EP2013/003161 on Oct. 21, 2013, now Pat. No. 9,743,914.

(30) Foreign Application Priority Data

Oct. 19, 2012   (EP) ..................................... 12007227

(51) Int. Cl.
*A61B 5/00*      (2006.01)
*A61B 10/02*     (2006.01)
*A61M 5/158*     (2006.01)

(52) U.S. Cl.
CPC .......... *A61B 10/0233* (2013.01); *A61M 5/158* (2013.01)

(58) Field of Classification Search
CPC ................ A61B 10/02; A61B 10/0233; A61B 2010/045; A61B 5/158; A61B 17/3417; A61B 17/3421; A61M 5/158
See application file for complete search history.

(56) References Cited

U.S. PATENT DOCUMENTS

| 4,946,442 | A | 8/1990 | Sanagi |
| 5,749,889 | A | 5/1998 | Bacich et al. |
| 5,921,918 | A | 7/1999 | Riza |
| 8,052,661 | B2 * | 11/2011 | McGuckin, Jr. ... A61B 17/3417 604/272 |
| 8,491,619 | B2 | 7/2013 | Breznock |
| 8,747,359 | B2 | 6/2014 | Pakter |
| 8,888,690 | B2 | 11/2014 | Swinehart |
| 8,939,960 | B2 * | 1/2015 | Rosenman ........ A61M 25/0045 604/526 |
| 9,108,020 | B1 | 8/2015 | Feloney |
| 9,125,639 | B2 | 9/2015 | Mathis |
| 9,247,929 | B2 | 2/2016 | Melsheimer |
| 9,743,914 | B2 * | 8/2017 | Brunner ............. A61B 10/0233 |
| 2005/0216018 | A1 | 9/2005 | Sennett |
| 2006/0189891 | A1 | 8/2006 | Waxman et al. |
| 2010/0298737 | A1 | 11/2010 | Koehler |
| 2012/0220894 | A1 | 8/2012 | Melsheimer |

* cited by examiner

*Primary Examiner* — Max Hindenburg
(74) *Attorney, Agent, or Firm* — MH2 Technology Law Group LLP

(57) ABSTRACT

The invention relates to a biopsy device comprising a needle extending longitudinally from a proximal end to a distal end and including a channel extending there through. At least one section (6) of the needle (3) is provided with a curved shape, so that tissues that normally would be out or reach of conventional needles can be targeted.

9 Claims, 6 Drawing Sheets

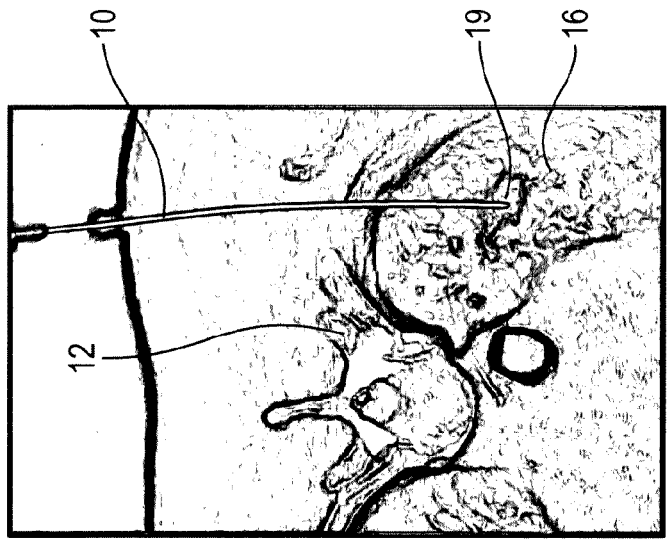
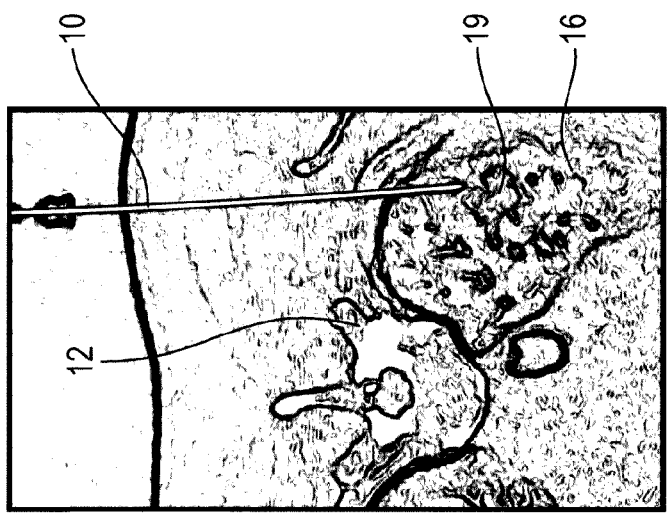
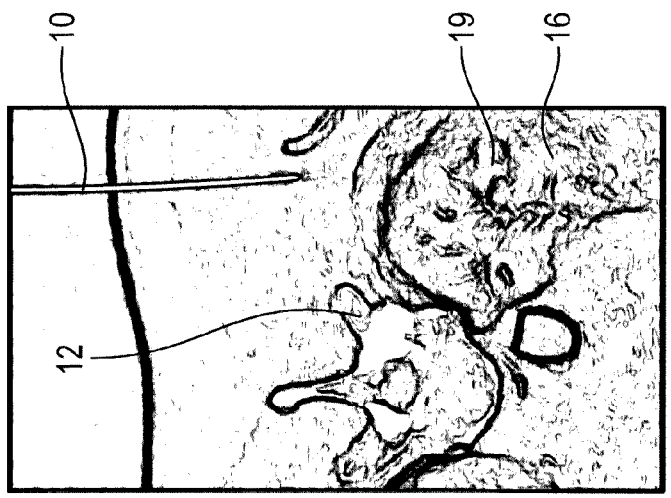
Fig. 3C
Fig. 3B
Fig. 3A

MEDICAL DEVICE COMPRISING A CURVED NEEDLE

CROSS-REFERENCE TO RELATED APPLICATIONS

This application is division of U.S. patent application Ser. No. 14/436,704, filed Apr. 17, 2015, which is a national-stage entry of PCT/EP2013/003161, filed Oct. 21, 2013, which claims priority to European Patent Application No. 12007227.7, filed Oct. 19, 2012, the contents of all of which are hereby incorporated by reference in their entirety.

TECHNICAL FIELD OF THE INVENTION

The invention relates generally to a medical device used in interventional radiology. Specifically, the invention relates to a medical device comprising a hollow needle extending longitudinally from a proximal end to a distal end and wherein the distal end of the hollow needle is formed as a cutting tip.

BACKGROUND OF THE INVENTION

Interventional radiology is a medical sub-specialty of radiology. It is a minimally-invasive image-guided procedure. It has been known to diagnose and treat diseases in almost every organ of the human or animal body. Today many medical conditions, for which conventional surgery would have been used in the past centuries, may be treated by interventional radiology. An interventional radiologist uses, inter alia, X-ray devices, computed tomography devices (CT), magnetic resonance imaging (MRI) devices, and ultrasonic imaging devices in order to obtain images of a human or animal body. As a consequence of these images, the interventional radiologist is able to navigate an interventional instrument throughout the body to a targeted organ or other part of the human or animal. Flexible catheters are inserted through a small nick in the skin and thus may be guided through a patient's network of arteries or veins. Where tissues of organs are not within reach of a catheter, a biopsy device comprising a rigid hollow needle is used to penetrate from the outside of the patient's body in a direct way to the target. Special instruments may be guided through the hollow needle to extract samples of the tissue, inject fluids, or slide radiofrequency ablation instruments to the target, for example, to destroy cancerous tissue locally in the targeted zone.

PRIOR ART

From U.S. Pat. No. 5,749,889 a surgical access device for endoscopic surgeries comprising biopsies or other surgical cutting procedures is known which comprises a substantially rigid channel extending to a curved distal end of the device. When a semi-rigid endoscope is inserted into the channel for viewing of the interior of the patient's body, the curves and bends direct the visualization area of the endoscope to preferentially view anatomical structures not on the axis of the insertion point in the body.

In contrast to the prior art, which relates to a hollow needle in respect of which the known insertion device does not provide a cutting tip, this invention not only provides for a cutting tip, but also provides for a wide variety of flexible, semi-flexible and spring type devices which are capable of being produced and manipulated in a wide spectrum of shapes so as to access a wide spectrum of organs or tissue in areas which are usually inaccessible without significant risk of harm to body organs or tissue.

Problem to be Solved by the Invention

Hitherto, the conventional use of hollow needles has been restricted to targeted organs or other parts of the human or animal body which are within reach of a straight trajectory. Often the target is behind a bone or organs that should not be touched. In such cases, the target is inaccessible for interventional radiology. The objective of the invention is to provide a hollow needle that permits access to targets that are inaccessible through use of conventional hollow needles.

SUMMARY OF THE INVENTION

In one aspect of the invention, the needle is pre-curved. As a consequence of the use of a curved needle, it is possible to effect a penetration via a curved penetration canal. This circumvents the obstacles which arise in the form of bones or other organs or elements or regions or zones of the body which must not be touched, such as blood vessels, the heart, the pleura, the trachea, the bronchi, or the esophagus, to name a few as an example.

In another aspect of the invention, wherein a curvature point around which the at least one section of the hollow needle is curved is substantially in the longitudinal axial plane of the needle which extends through a culmination point of the cutting tip (8), and wherein in relation to the longitudinal axis of the hollow needle the curvature point is on the same side as the culmination point of the cutting tip. This design of the needle provides a bevel of the cutting tip to be located on the opposite side of the curvature center in respect to the longitudinal axis of the needle. The at least one bevel thus is on the convex side of the needle. When an appropriate force is applied to the needle the at least one bevel springs of the tissue and guides the cutting tip in direction of the end point of the cutting tip, e.g. in direction of the virtual curvature center. This configuration enables the operator to force the needle into a smaller curvature than that of the pre-arranged radius of the said needle.

In another aspect of the invention, the cutting tip is cut at an angle of at least 45 degrees relative to the longitudinal axis of the hollow needle. An angle that is at least 45 degrees enables the needle when a force on the handle, respectively the proximal end of the needle is applied into a single, specific direction to be forced into a curved trajectory. In another aspect of the invention, the needle is sufficiently rigid to keep its form when penetrating through body tissue, and at the same time is sufficiently flexible that it can be temporarily forced into another form.

Preferably the material properties of the needle are chosen such that the needle substantially returns to its curved form after the needle has been forced temporarily into another form. The rigidness depends on the material properties of the needle, such as, for example, the substance of which the needle is made, the thickness of the needle and the thickness of the needle walls. A needle that is flexible enough to allow small deformations but would return to its original shape once the deforming forces are released, has the consequence of allowing the needle to be straightened whilst embedded in the body tissue by a simple turn of the needle by the operator. Once the needle is turned back to its original angle of attack, the needle takes substantially its original curved form, so that it is possible to continue the penetration with a curved trajectory. By applying appropriate turns the needle may be forced even into a S-shaped trajectory.

DESCRIPTION OF THE FIGURES

FIG. 3A-3C show the use of the curved needle in another treatment of the lung

DETAILED DESCRIPTION OF THE INVENTION

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

Figure 1A:
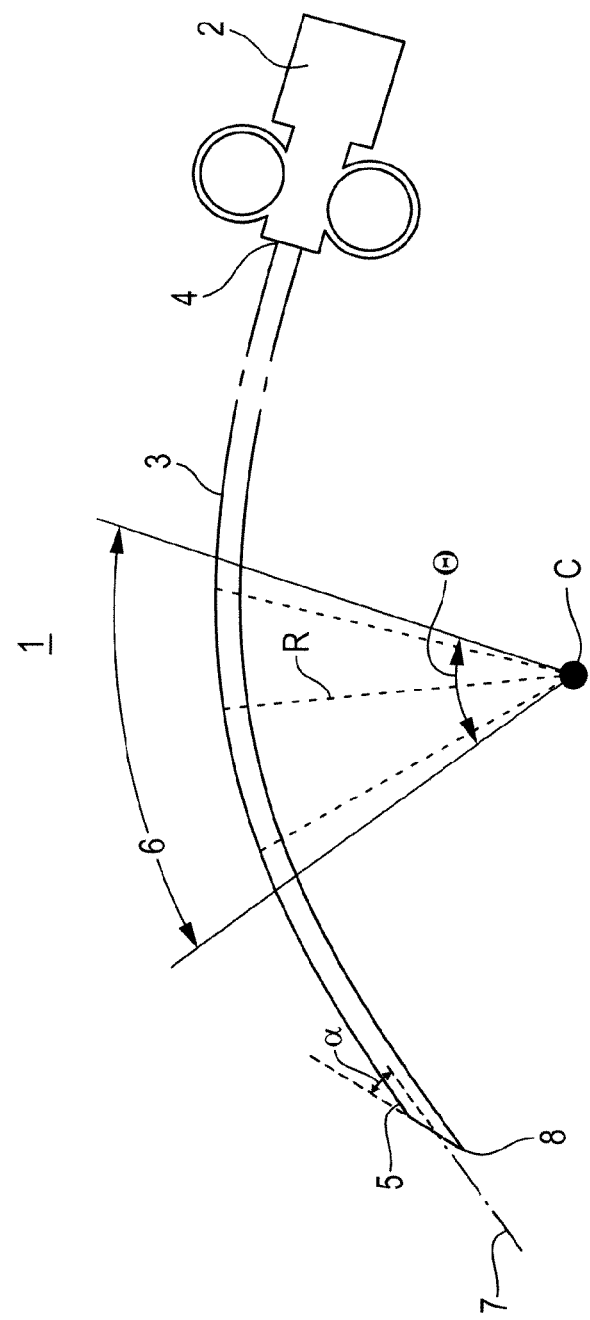
FIG. 1A shows a medical device with a curved needle
Figure 1B:
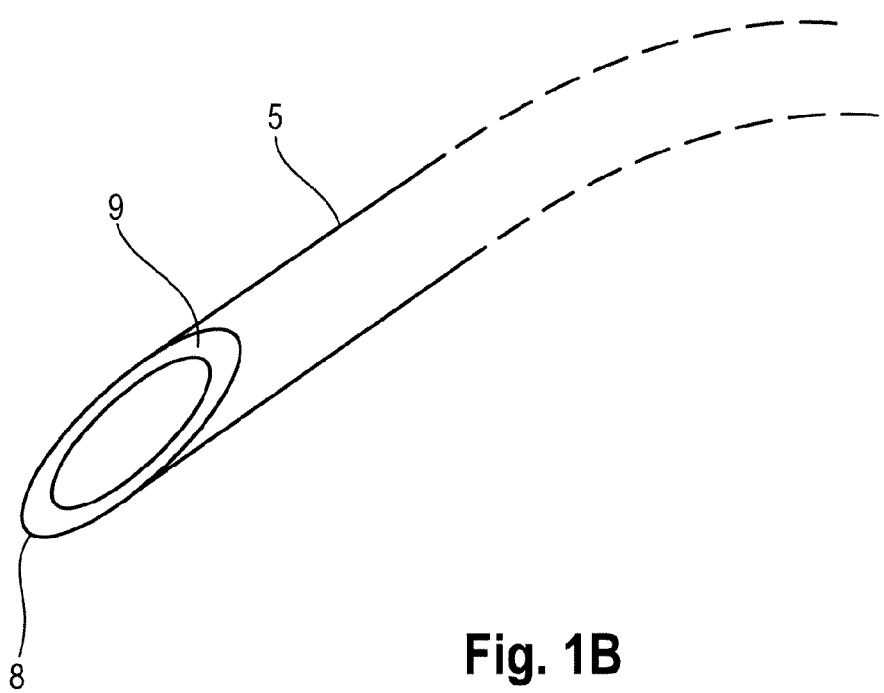
FIG. 1B shows the distal end of the needle

FIG. 1 shows a medical device 1 for percutaneous biopsy with a handle 2 and a hollow needle 3. The handle 2 facilitates manipulations by an operator of the needle 3 and may for example include finger grips. The needle 3 extends from a proximal end 4 to a distal end 5 and includes a lumen extending there through. It should be noted that the terms "proximal" and "distal", as used herein, are intended to refer to a direct toward (proximal) and away from (distal) an operator of the biopsy device 1. The distal end 5 is cut at an angle α relative to the longitudinal axis 7 of the needle 3 forming a distal tip 8 (FIG. 1b) and a bevel 9 (FIG. 1b) extending there around. The distal tip 8 and the bevel 9 facilitate the penetration of the distal end 5 into tissue.

At least a section 6 of the needle 3 has a curved shape around a virtual curvature center C. In case the section 6 corresponds substantially to a circular arc the distance between the virtual curvature center C and the needle 3 corresponds to a radius R of this circular arc and the section 6 of the needle 3 forms a segment of the circular arc extending over a central angle θ. Alternatively the full length of the needle may be curved. As a function of the dimensions of the organs and bones of the person to be treated and the task to be achieved needles may be manufactured and offered with different curvature radius R and center angles θ. Accordingly also the shape of the curved section 6 may vary. The shape could be, but is not limited to, a segment of a circle as described, a segment of an ellipse, a segment of a parable or a segment of a hyperbole. The shape may vary from any of these forms. The idea of the curved section 6 of the needle 3 is to allow penetration of tissue in a curved trajectory.

The needle may be formed of, for example, a polymer, stainless steel, alloys or any combination of materials that are suitable to achieve the appropriate rigidness of the needle. The needle is hollow, i.e. comprises a lumen through which cutting devices or other devices may be applied. The term rigid has to be understood to express that the needle is sufficiently rigid so as to be not deflected by effect of impact upon the human or animal tissue, when the needle is injected in and pushed through the tissue. The needle will keep its curved form to a large extent. For some applications, the material and the dimensions of the rigid needle may be chosen so that on the one hand it is able to yield appropriately under pressure, yet on the other hand is sufficiently flexible to regain at least partially its initial curvature when the pressure is released.

Ideally the plane of the curvature is chosen such that the distal tip 8 of the needle 3 substantially lies in the plane of the curvature and that the distal tip 8 is on the same side of the needle 3 as the curvature center C in respect to the longitudinal axis 7 of the needle 3. This configuration makes it easier to force the needle into a curved trajectory through the body tissue.

In preparation of the intervention, a patient is placed under an imaging device (not shown) such as an X-ray device, a Computer Tomography device (CT), or a Magnetic Resonance Imaging device (MRI). The term patient is used to describe a human or an animal that is treated by interventional radiology.

Figure 2A:
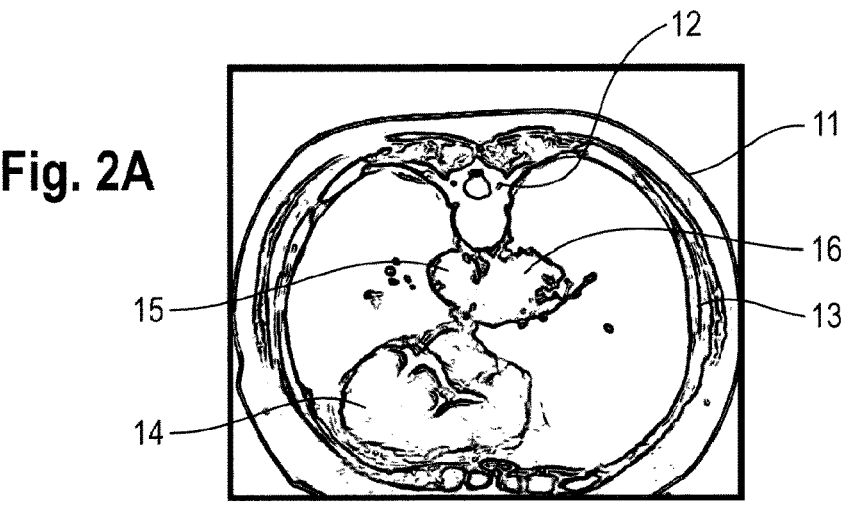
FIG. 2A-2C show the use of the curved needle in a treatment of the lung
Figure 2B:
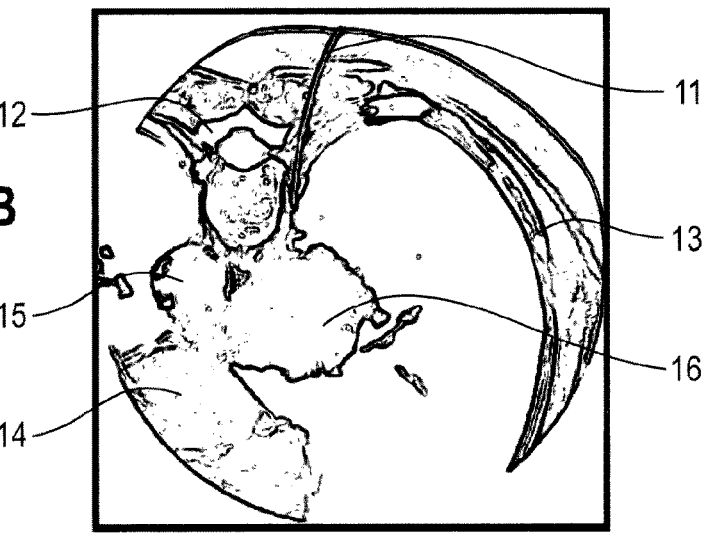
Figure 2C:
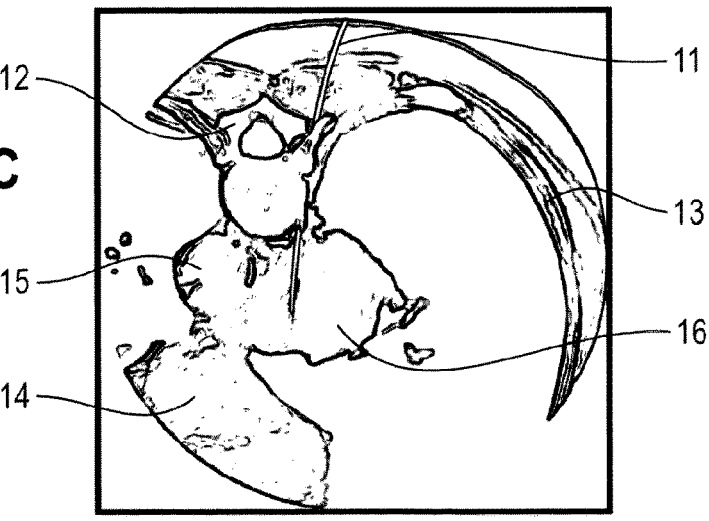

FIG. 2A to 2C show the use of a curved needle 10 for a treatment of a human body. The FIGS. 2A-2C represent real images that are displayed to an operator on his or her screen. For formal requirements of patent drawings the colour of the real images have been inverted in FIGS. 2, 3 and 4. The operator will see in a transversal section of the patient a vertebra 12, ribs 13, a heart 14, an aorta 15 and lung tissue 16. Usually lung tissue cannot be seen on an X-ray device. The lung tissue 16 that is depicted on the FIGS. 2A-2C has been made visible by applying a radiocontrast agent. Therefore only that part of the patient lung can be seen that is affected by the radiocontrast agent.

FIG. 2A shows the situation when an operator positions the needle 10 at the skin 11 of the patient. As the needle 10 is in front or behind the plane of the X-ray, the needle 10 that is outside the patient's body cannot be seen on most of the figures. In the following, the term operator is used to describe the person who manipulates the medical device 1. In most cases this person would be a radiologist with special knowledge in intervention with needles. By pushing the handle 2 of the medical device 1 the tip 8 of the needle 10 cuts through the skin 11 and penetrates through the patient's body. The operator follows the advancement of the needle 10 by requesting images from the imaging device and watching these images on a screen. The needle 10 usually gives a clear image on the screen.

FIG. 2B shows that the needle 10 was entered between the endothoracic fascia and the parietal pleural membrane. With a conventional needle, access would be restricted to tissue that is straight below this access point. By means of the curved needle 10 it is however possible to direct the needle 10 to a region that would normally be out of reach (FIG. 2C).

As the distal tip 8 is on the same side of the longitudinal axis as the curvature center C, the needle can be pushed in a narrower curve than the actual radius of the curvature. In order to achieve this goal the operator has to guide the needle 10 such that the convex side, e.g. the tip 8 of the needle that is opposite to the curvation center C in respect of the longitudinal axis 7 of the needle, is pushed with its bevel 9 (FIG. 1B) against the body tissue. The edge of the needle 10 props against this counterforce and is forced into a smaller curvature. In this respect it has been observed that the cutting angle, i.e. the angle α between the longitudinal axis 7 and the plane spanned by the bevel 9 should be flat, e.g. substantially 45 degree or less. A cutting angle α that is at least 45 degrees facilitates the needle to be forced into a curved trajectory when a force on the handle 2, respectively the proximal end 4 of the needle 3 is applied.

When the needle is in the intended place the operator in case the medical device 1 is a biopsy needle may either insert through the handle 2 a cutting tool to collect a tissue sample from the targeted region. The biopsy needle may also be used to insert instruments for treatment. For example an electrode (not shown) by which the region around the needle tip is heated in order to destroy the tissue around the needle tip, for example by applying radio frequencies. In case the medical device is an infiltration needle it may be used to inject a toxic substance that locally kills the cancer cells.

FIGS. 3A-3C are photos taken at different instants. In reality the patient is breathing and especially the patient's lung is moving. In FIG. 3A the curved needle has approached a cancerous nodule 19 of the lung tissue 16. Due to the breathing of the patient the nodule 19 is moving. The operator takes the tip of the needle 10 closer to the nodule 19 (FIG. 3B). By little turns of the curved needle 10 the operator is able to position the tip of the needle such that nodule 19 drives itself into the tip of the needle 10 when the patient is breathing (FIG. 3C). With a straight needle it is only possible to retract or to push forward whereas the curved needle is able to turn like a key in a lock. With this kind of movement it is significantly easier to anticipate the movement of the nodule with the curved needle.

Figure 4A:
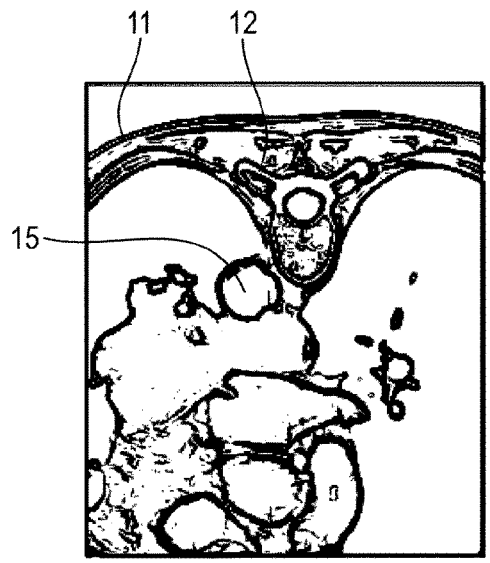
FIG. 4A-4F show the use of two curved needle in a treatment of the lung
Figure 4B:
Figure 4C:
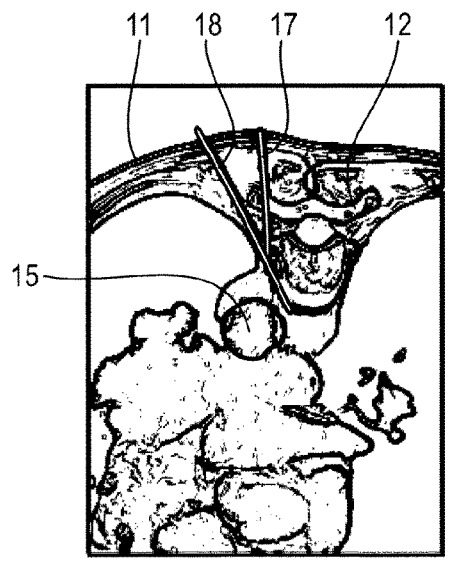
Figure 4D:
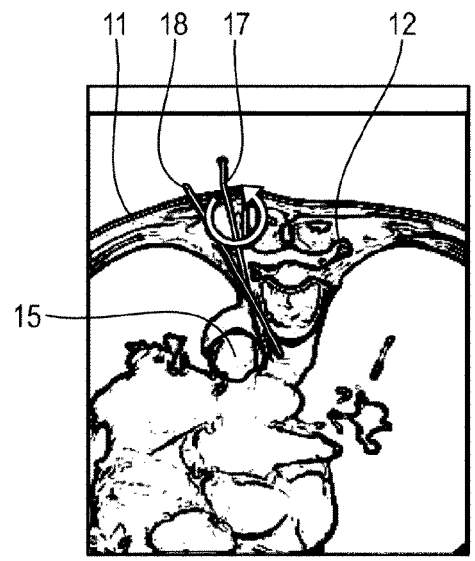
Figure 4E:
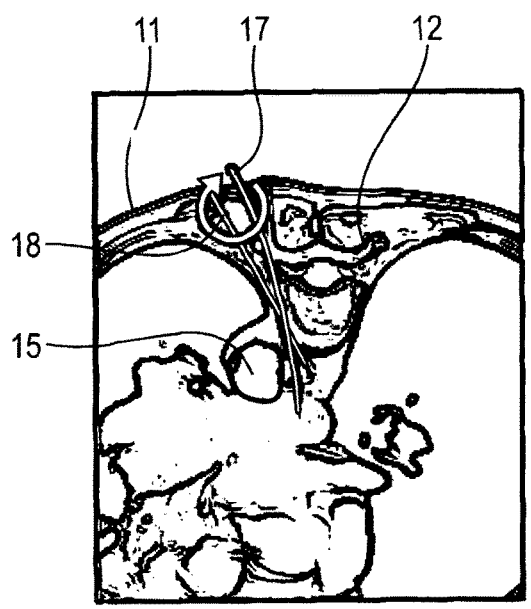
Figure 4F:
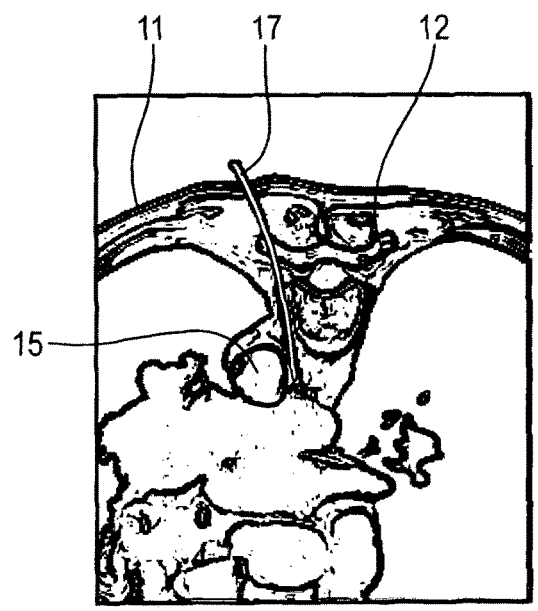

In another aspect of the invention the needle possesses sufficient rigidity to reverse back to its original curved form, even when it is forced temporarily into another shape. FIG. 4A-FIG. 4F show another aspect of the invention making use of this property of the curved needle according to the invention. A first needle 17 is entered between the endothoracic fascia and the parietal pleural membrane so that a tip of the first needle 17 is extending away from the vertebra (FIG. 4B). FIG. 4C shows the insertion of a second needle 18 through the canal of the first needle aiming between the aorta 15 and the vertebra 12. Through the second needle 17 a volume of 15 ml of serum is injected. After the injection of the serum the second needle 18 is retracted. The serum creates a little volume of serum that pushes the aorta to the side, so that more space for the movement of the first needle is created. The first needle 17 is then turned anti-clockwise by 180° so that the curved part is now following the shape of the vertebra (FIG. 3D). The first needle is pushed deeper and then turned back clockwise by 180° after the tip of the first needle has passed the aorta 15. Due to the curved section of the first needle 17, when the first needle 17 is pushed further into the body tissue or organ, it follows a trajectory that aims at a target that usually would have been blocked by the aorta 15.

The treatment with curved needles is especially advantageous in cases of mediastinum lymphadenopathy, abdominal pulmonary masses, small pulmonary nodules and intra- or retroperitoneal masses. The advantages in case of the pulmonary nodules has been already discussed above.

The medical device 1 comprising the curved needle 3 has been presented in the course of treatment of cancer. The person skilled in the art however will appreciate that this is an example only and that the curved needle may be used for other purposes and is not limited to treatment of cancer at all.

The invention claimed is:
1. A method of operating a medical device, comprising: inserting the medical device into tissue, wherein:
   the medical device comprises a hollow needle,
   the hollow needle extends longitudinally from a proximal end to a distal end,
   the hollow needle comprises a straight section proximate to the distal end and a curved section between the straight section and the proximal end,
   the distal end of the hollow needle has a cutting tip,
   the curved section of the hollow needle has a first curvature prior to being inserted into the tissue, and
   the curved section of the hollow needle is configured to have a second curvature that is less than the first curvature when passing through the tissue without having a tool or instrument positioned within the hollow needle.

2. The method of claim 1, further comprising:
reducing a radius of curvature of the hollow needle by forcing a bevel of the cutting tip against the tissue; and
increasing the radius of curvature after decreasing the radius of curvature by rotating the hollow needle.

3. The method of claim 1, further comprising inserting a tool or instrument through the hollow needle when the hollow needle is in an intended place in the tissue.

4. The method of claim 3, wherein the tool or instrument comprises a second needle.

5. The method of claim 4, further comprising:
injecting a fluid through the second needle, wherein the fluid moves an object in the tissue to create more space for movement of the hollow needle; and
retracting the second needle after the fluid has been injected.

6. The method of claim 5, further comprising:
rotating the hollow needle after the fluid has been injected; and
pushing the hollow needle at least partially past the object after the hollow needle has been rotated.

7. The method of claim 6, further comprising rotating the hollow needle back after the hollow needle is pushed at least partially past the object.

8. The method of claim 1, further comprising injecting a fluid through the hollow needle when the hollow needle is in an intended place in the tissue.

9. The method of claim 8, wherein the fluid comprises a toxic substance designed to kill cancer cells in the tissue.

* * * * *